US006326183B1

(12) United States Patent
Barsoum

(10) Patent No.: US 6,326,183 B1
(45) Date of Patent: Dec. 4, 2001

(54) CHROMATOGRAPHICALLY CONCENTRATED BACULOVIRUS AND METHODS

(75) Inventor: James G. Barsoum, Lexington, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/537,631

(22) Filed: Mar. 29, 2000

Related U.S. Application Data

(63) Continuation of application No. PCT/US98/21102, filed on Oct. 7, 1998.
(60) Provisional application No. 60/065,554, filed on Nov. 14, 1997, and provisional application No. 60/061,625, filed on Oct. 9, 1997.

(51) Int. Cl.[7] .............................. C12N 7/02; C12N 7/01
(52) U.S. Cl. .................... 435/239; 435/235.1; 435/320.1
(58) Field of Search .................. 435/239, 235.1, 435/320.1

(56) References Cited

U.S. PATENT DOCUMENTS

| 5,447,859 | 9/1995 | Prussak | 435/239 |
|---|---|---|---|
| 5,871,986 | 2/1999 | Boyce | 435/320.1 |

FOREIGN PATENT DOCUMENTS

| 0 884383 A1 | 12/1998 | (EP) . |
|---|---|---|
| WO 96/27677 | 9/1996 | (WO) . |
| WO 97/32010 | 9/1997 | (WO) . |

OTHER PUBLICATIONS

Bowles et al., 1996, Human Gene Therapy, 7:1735–1742, "A Simple and Efficient Method for the Concentration and Purification of Recombinant Retrovirus for Increased Hepatocyte Transduction in Vivo".
Goswami et al., 1991, Biotechniques, 10:5:626–630 "A Simplified Method for the Production of Recombinant Baculovirus".
Huyghe et al., 1995, Human Gene Therapy, 6:1403–1416, "Purification of a Type 5 Recombinant Adenovirus Encoding Human p53 by Column Chromatography".
Kitts et al., 1993, BioTechniques, 14:5:810–817, "A Method for Producing Recombinant Baculovirus Expression Vectors at High Frequency".
Sandig et al., 1996, Human Gene Therapy, 7:1937–1945, "Gene Transfer into Hepatocytes and Human Liver Tissue by Baculovirus Vectors".
Boyce et al., 1996, Genetics, 93:2348–2352, "Baculovirus–mediated gene transfer into mammalian cells".
Zanotto et al., 1993, J. of Invertebrate Pathology, 62:147–164, "Phylogenetic Interrelationships among Baculoviruses: Evolutionary Rates and Host Associations".
Hofmann et al., 1995, Cell Biology, 92:10099–10103, "Efficient gene transfer into human hepatocytes by baculovirus vectors".
Chapts 1–3, Baculovirus Expression Vectors: A Laboratory Manual, O'Reilly, Miner and Luckow (1994) Oxford Univ. Press.

*Primary Examiner*—Mary E. Mosher

(57) ABSTRACT

A protocol for the ion exchange concentration of baculovirus is presented.

21 Claims, No Drawings

CHROMATOGRAPHICALLY CONCENTRATED BACULOVIRUS AND METHODS

RELATED APPLICATIONS

This application is a continuation under 35 U.S.C. §120 of PCT/US98/21102, filed on Oct. 7, 1998, which claims priority under 35 U.S.C. §119(e) to Provisional Application No. 60/061,625 filed on Oct. 9, 1997 and Provisional Application No. 60/065,554 filed on Nov. 14, 1997.

BACKGROUND OF THE INVENTION

Baculovirus are a diverse group of viruses having a host range which is restricted to insects. They are large viruses having a lipid envelope and containing a genome of double-stranded circular DNA. Recombinant baculovirus (rBV) vectors, primarily derived from the baculovirus *Autographa californica* multiple nuclear polyhedrosis virus (AcMNPV), are commonly used in industry and academia for the high-level production of heterologous proteins in insect cells. This expression system involves the infection of cultured insect cells with rBV into which the gene encoding the protein to be expressed has been inserted. See O'Reilly, D. R., Miller, L. K., and Luckow, V. A. (1992) *Baculovirus Expression Vectors: A Laboratory Manual.* (Freeman, New York) for review of the baculovirus expression system.

Another potential use of rBV has recently appeared. It is demonstrated that rBV can transfer genetic material into mammalian cells, with a preference for hepatocytes. As long as a gene of interest is preceded by a promoter that is active in mammalian cells, the gene will be efficiently expressed in the target mammalian cells. See Hofmann, C., Sandig, V., Jennings, G., Rudolph, M., Schlag, P., and Strauss, M. (1995), "Efficient gene transfer into human hepatocytes by baculovirus vectors", *Proc. Natl. Acad. Sci. USA* 92, 10099–10103; Boyce, F. M. and Bucher, N. L. R. (1996) "Baculovirus-mediated gene transfer into mammalian cells", *Proc. Natl. Acad. Sci. USA* 93, 2348–2352, incorporated herein by reference. This previously unobserved characteristic makes rBV potentially useful in human gene therapy. Recombinant baculovirus has several potential advantages for gene therapy. These include:

1. a very large DNA insert capacity
2. A fairly high viral titer
3. absence of a pre-existing immune response in humans
4. lack of replication in mammals
5. lack of toxicity in mammals
6. lack of expression of viral genes in mammalian cells due to the insect-specificity of the baculovirus transcriptional promoters, and, therefore, a potential absence of a cytotoxic T lymphocyte response directed against these viral proteins Nevertheless, there exists a need for a method to concentrate rBV to a very high titer. This will be required for in vivo gene therapy applications of high doses of rBV. This virus must be at high titer and must be present in a physiological buffer. Also, a purification/concentration step is critical in large scale in vitro production of proteins in insect cells. In order to produce proteins at very high levels, the insect cells must be infected with rBV at a high multiplicity of infection (moi). If the rBV has not been previously concentrated, but is rather simply the conditioned medium from the insect cells producing the virus, the volume of the inoculum would be a significant proportion of the total bioreactor volume. This may not be desirable, nor in some cases even possible, in large-scale manufacturing.

Viruses are conventionally concentrated to high titer by a combination of pelleting the virus through use of an ultracentrifuge and by banding the virus in, for instance, a sucrose gradient. See, for example, Sandig, V., Hofmann, C., Steinert, S., Jennings, G., Schiag, P., and Strauss, M. (1996) "Gene transfer into hepatocytes and human liver tissue by baculovirus vectors", *Human Gene Therapy* 7: 1937–1945 and Bowles, N. E., Eisensmith, R. C., Mohuiddin, R., Pyron, M. And Woo, S. L. C. (1996) "A simple and efficient method for the concentration and purification of recombinant retrovirus for increased hepatocyte transduction in vivo", *Human Gene Therapy* 7: 1735–1742. Unfortunately, rBV preparations made in this manner tend to be badly aggregated (See Example 1). Therefore, a concentration step is needed that avoids this problem, but such a step has not heretofore been available.

SUMMARY OF THE INVENTION

In accordance with this invention, there is provided a process for producing chromatographically concentrated baculovirus, which process comprises contacting a preparation containing a baculovirus with an ion exchange chromatographic resin and eluting the bound baculovirus from the resin.

Briefly stated, the present invention provides methods to separate lipid envelope viruses, e.g., baculoviruses, from preparations. In one aspect, the present invention provides methods for the separating a baculovirus from contaminating substances comprising the steps of: (a) contacting a preparation containing a baculovirus with an ion exchange chromatographic resin, so that the virus binds to the resin and (b) eluting the bound baculovirus from the resin in a volume that is smaller than that of the original starting volume. The method may further include the step of separating from the resin, prior to the elution step, that portion of the preparation which is not bound to the resin.

In another method, the resin is generated in buffer and, after the resin is contacted with the baculovirus but before the elution step, the resin is washed with a buffer having properties identical to the buffer used to generate the resin. Preferred resins include those comprising derivatized agarose in which the derivative is at least one aryl sulfate group or a sulfopropyl group. Additional resins include those selected from the group consisting of: (i) a mixed resin column of silica derivatized with mixed cationic and anionic groups; (ii) a silica resin comprising carboxyl and sulfate functional groups; (iii) a cellulose resin with a carboxymethyl functional groups; (iv) an acrylamide resin with carboxymethyl functional groups; (v) a ceramic resin with sulfate functional groups and (vi) a sepharose resin with carboxymethyl functional groups.

A further aspect of the invention is a chromatographically concentrated preparation of baculovirus having the following properties: (a) concentrated at least five fold from an original preparation; (b) having less than about 50% soluble protein, exclusive of viral protein, and (c) in contact with a physiological buffer. Another chromatographically concentrated preparation of baculovirus has the property of lacking significant aggregation when tested by centrifugation at about 4000 g for about 6 minutes.

The method presented is an easy and rapid single step concentration using column chromatography. This protocol has advantages over other methods in that no ultracentrifugation is required, the virus does not appear to aggregate appreciably during the concentration and the method can be easily scaled up to a very large size.

DETAILED DESCRIPTION OF THE INVENTION

This invention is based, in part, on the discovery that protein purification schemes using column chromatography can be applied to the purification and concentration of baculovirus. In particular, we are now able to generate "chromatographically concentrated baculovirus" using ion exchange chromatographic procedures, defined as baculovirus that has been concentrated by a factor of at least five, preferably ten to thirty, most preferably about fifty to one hundred fold, over a titer of baculovirus prior to the chromatographic procedure. Moreover, a chromatographically concentrated" preparation has a protein concentration, exclusive of viral protein, having a value reduced to less than 50% of its original protein concentration. A further property of a chromatographically concentrated preparation is that at least fifty (50%) percent of the baculovirus is in a non-aggregated state as compared to the baculovirus preparation prior to the chromatographic procedure. The term "non-aggregated state" refers to the ability of the baculovirus in the chromatographically concentrated preparation not to form pellets under low speed (e.g., no greater than about 4000 g) centrifugation. That is, that portion of the viral preparation remaining in the supernatant after low speed centrifugation is the "non-aggregated" portion.

The term "ion exchange chromatography resin" refers to a matrix whose components carry functional groups that have either positive or negative charges (anion-exchangers and cation-exchangers, respectively). Under normal conditions, these charges are balanced by counterions. Under appropriate conditions of pH and ionic strength, materials are added to the column, such that some or all of the materials become bound by interactions between the surface charge of the material and the charge carried by the ion exchanger. By gradually changing the chemical properties of solvent passing through the column, the bound materials may be released from the column.

Generally speaking, strong anion exchange resins have a support matrix that is derivatized by a quaternary amine or quaternary aminoethyl group. Weak anion exchangers are typically derivatized by a diethylaminoethyl (DEAE) group or a polyethyleneimine group. Strong cation exchangers are typically derivatized by an aryl sulfate such as sulfopropyl or by sulfonic acid. Weak cation exchangers are characterized as having, for instance, carboxymethyl functional groups.

The many types of resins that can be used in the present methods can be divided into polysaccharide-based, silica-based and styrenic or acrylic polymer-based supports. The preferred polysaccharide-based materials used in the present method may include an anion exchange resin of cross-linked agarose with a quaternary amine functional group with a particle size ranging from about 10 to about 200 micrometers. The cation exchange resin is preferably a sulfopropyl-derivatized sepharose. Other exemplary ion exchangers include diethylaminoethyl-derivatized cellulose (anionic) and the weak cation exchanger carboxymethyl-derivatized cellulose (CM).

Most silica-based resins contain the above-identified functional groups bound to the silica surface by siloxane bridges. Most styrenic or acrylic resins are made of methacrylate copolymers, acrylic polymers or cross linked polystyrene/divinylbenzene copolymers (PS/DVB). When functionalized with sulfonic acid and quaternary amine moieties, the PSIDVB resins act as cation and anion exchangers, respectively. These same resins can be functionalized with CM to produce weak cation exchangers. A partial list of commercial ion exchangers useful in the present methods can be found in Choudhary and Horvath, "Ion-Exchange Chromatography" Section I, Chapter 3, in *Methods in Enzymology*, Volume 20, (ed., Karger and Hancock), Academic Press, 1996, the entire contents of which are incorporated herein by reference.

As described herein, baculovirus can be concentrated using a wide variety of ion exchange resins. We successfully employed ion exchange resins containing functional groups on a Sepharose support resin (See Examples 2–5). We also have found that other resins such as cellulose, acrylamide, silica and ceramic also work in the present protocol. We used several columns to successfully concentrate the baculovirus Z4, including: (a) mixed resin silica columns containing, among other groups, carboxyl and sulfate functional groups; (b) a cellulose resin with a carboxymethyl functional group; (c) a acrylamide resin with carboxymethyl functional groups and (d) a ceramic resin with a strong cationic group, probably sulfate (See Example 7).

A key feature of the present method is that we wished to generate high titer rBV in one simple step which will leave the virus in a relatively non-aggregated form in a physiological buffer. We found that rBV, as an enveloped virus, clearly aggregates into large clumps whenever ultracentrifugation is performed. As a crude assay for aggregation, we performed a low speed centrifugation (4000 g for 6 minutes in a table-top Eppendorf microfuge). We found that rBV concentrated by ultracentrifugation is virtually completely pelleted by this low speed spin (99.9% of virus in the pellet), indicating that it is aggregated into significantly large clumps (See Example 1). Significantly, ultracentrifugation steps cannot be readily scaled-up.

The protocol described in this application uses column chromatography to concentrate rBV to high titer in a single step. This method leaves the virus in a physiological buffer, does not lead to virus aggregation, and can be scaled up.

A. Virus production

A preferred use of the present method is the concentration of enveloped viral-based gene therapy vectors, particularly baculovirus vectors. Nevertheless, any enveloped virus is a candidate for purification using the present methods. As used herein, the term "virus" includes DNA viruses, RNA viruses, envelope viruses, and viral vectors. Suitable lipid envelope viruses, such as HIV, murine retrovirus, herpes, and certain enveloped hepatitis viruses may be used. Particularly preferred viruses are the baculoviruses.

Construction of baculovirus vectors, generation of virus stocks and assay of virus by plaque titering are all done by conventional methods. See, for example, O'Reilly, D. R., Miller, L. K., and Luckow, V. A. (1992) *Baculovirus Expression Vectors: A Laboratory Manual*. (Freeman, New York); and Kitts, P. A. and Possee, R. D. (1993), "A method for producing recombinant baculovirus expression vectors at high frequency", *BioTechniques* 14: 810–817. incorporated herein by reference. The Kitts and Possee system was used to generate baculovirus Z4 (Boyce and Bucher, 1996, supra) used in these studies.

Briefly, the system provides a selection for recombinant viruses by using a gene essential for viral replication downstream of the baculovirus expression locus. The expression locus and part of the downstream gene are flanked by restriction sites that do not occur elsewhere in the viral DNA. Certain pieces of the viral genome are restricted out. Co-transfection is then initiated with the "restricted" virus (missing essential pieces of the viral genome) and a transfer vector carrying an intact copy of the missing viral genome downstream from a site into which foreign genes are inserted for expression. Homologous recombination between the "restricted" parental viral DNA and the transfer vector yields recombinant viral expression vectors carrying the foreign gene flanked by the expression locus and a fully reconstructed gene necessary for viral replication.

The Z4 virus can be propagated in insect cells and is shown to express high levels of the β-galactosidase gene (directed by the Rous sarcoma virus long terminal repeat promoter) after transduction of human hepatoma cells and primary rat hepatocytes (Boyce and Bucher, supra). The expressed β-galactosidase protein is useful in that its production level can be assayed easily by staining of the transduced cells or by a quantitative chemiluminescence assay.

Z4 virus preparations are generated by infection of the insect cell line Sf9 (American Type Culture Collection). Any other insect line which is commonly used for baculovirus production would also be effective. Among these lines are Sf21 and High Five (both available from Invitrogen, San Diego, Calif.).

It will be evident to those of ordinary skill in the art that the capacity of a candidate virus to bind to a cation or anion exchange resin may be readily tested. For example, a virus containing preparation may be contacted with a cation exchange resin, the resin washed to remove unbound virus, and the amount of virus in the wash compared to the amount of virus in the initial preparation.

B. Concentration and Separation Schemes

A virus may be concentrated from a variety of types of preparations. For example, a cell free supernate which contains a virus can be the preparation. Alternatively, a virus may be concentrated from other preparations, such as blood products. Specifically, baculovirus may be concentrated from a preparation of insect larvae.

The methods of the invention may be used in a variety of formats in the concentration of a virus. For example, an ion exchange chromatography resin may be placed in a column, the resin being the solid phase column matrix. A virus containing preparation is passed through the column and the virus adsorbs to the resin. It will be appreciated by those of ordinary skill in the art that optimization of column performance is dependent upon sample volumes and flow rates. Substances in the preparation that do not bind to the resin will pass through the column. For example, many proteins, lipids and carbohydrates will not bind to ion exchange resins under well defined conditions. It may be desirable to optionally wash the column one or more times to ensure that all unbound substances have been removed. This is typically accomplished by generating the resin in a particular buffer and using this same buffer to wash the column. Moreover, prior to elution of the virus, it may also be desirable to wash the column with a solution having a pH different than the application pH strength, but less than that required to elute the virus in order to remove any substances weakly bound to the column.

The virus which is bound to the resin is de-adsorbed from the column by using a buffer of different pH value than that found in the culture medium.

It will be evident to those of ordinary skill in the art that use of a ionic exchange resin in the concentration of a virus may be performed in combination with other concentration techniques, such as standard chromatographic techniques. Such techniques include, for example, gel filtration chromatography, size exclusion and affinity chromatography. In a multi-step procedure, a step utilizing an ion exchange resin may be the initial step, final step, or be interposed between other steps, and may be repeated.

An alternative to the use of column chromatography is the use of a batch format. For batch applications, a ion exchange resin can be added directly to a virus containing preparation. To maximize the interaction of the resin with a virus, the reaction mixture should be gently agitated. Following virus adsorption to the resin, the portion of the preparation which is not bound can be separated from the virus containing resin in a variety of ways. For example, the resin may be separated by centrifugation (e.g., 1000 g for 5 min.), filtration or settling (e.g., 2 hr. at 1 g). The virus which is bound to the resin is de-adsorbed by using a buffer having a pH value that is different that the pH value of the baculovirus growth or culture medium. In addition, as described above, it may be desirable to wash the resin with one or more solutions prior to elution of the virus.

Monitoring for the presence of virus in column or batch eluates may be performed by a variety of techniques. Such techniques include plaque assays and colony forming unit (CFU) assays, such as those described herein.

Baculovirus in particular may be concentrated through the use of a variety of different chromatographic methods including ion exchange, size exclusion and affinity purification.

The preferred method, however, uses an ion exchange chromatography resin, relying on the net charge of the virus at a given pH value to provide the separation/concentration function.

The Example given below uses a cation exchange column, in particular a strong cation exchanger such as an "SP" column (SP Sepharose Fast Flow; Pharmacia Biotech; cat. #71-7065-00). This material is attractive in that only ~10% of total proteins will bind to the column under the conditions employed. The general strategy is to load the virus onto the column at a low pH and then elute the virus from the column by treatment with a higher pH solution. The virus has a net positive charge at the low pH and will bind to the column very well. This is because the SP material ionizes to negatively charged species that hold the positively charged (i.e., cationic) virus. At the higher pH, the virus is less positively charged and will wash off the column.

The conditioned medium from the Z4-producing insect cells is acidic (pH 5.9). The pH of virus prepared in both Sf-900 II SFM and Grace's medium/10% FBS (both obtainable from Gibco BRL) is approximately equivalent. If a higher pH medium is employed for virus production, the pH of the conditioned medium could be lowered by the addition of any number of buffers such as phosphate buffer or an organic buffer (such as 1M MES, pH 5.5 to 5.8) to a final concentration of 25–50 mM just before loading the virus onto the column.

We also have concentrated Z4 virus through use of a Q Sepharose Fast Flow column (Pharmacia Biotech; cat. #71-7070-00), which is a strong anionic exchanger. We increased the pH of the conditioned medium prior to loading the column with the baculovirus preparation and then eluted the column at a pH less than that of the medium. See Example 3.

Other column chromatography methods may be employed. Among these are size exclusion and affinity chromatography (using a monoclonal antibody directed against baculovirus surface protein or rabbit polyclonal antibody raised against baculovirus).

Another use of methods of the present invention is the removal of virus which is contaminating a preparation. Such preparations include biological samples, such as antibody samples, blood, biologic products, and other biopharmaceutical products. Similar to its use in concentration, a ion exchange resin may be used in a variety of formats for the removal of a contaminating virus from a preparation. For example, a resin may be placed on a column or added directly to a preparation in a batch procedure. A preparation suspected of containing a virus is contacted with an ion exchange resin to allow a virus to bind to the resin. For example, where a cation exchange resin is added directly to a preparation, the combination is typically allowed to mix for about 30 min. at about room temperature while gently stirred. Following binding, the preparation and resin are separated. For example, where a resin as described above is added directly to a preparation, the portion of the preparation which is not bound to the resin may be separated from the resin by a variety of means, including centrifugation, filtering and settling. It will be evident to those of ordinary skill in the art that the binding and separation steps may occur simultaneously. For example, where an ion exchange resin is used in a column, the preparation flows through the column to effect both binding of a virus to the resin and separation of the portion of the preparation which is not bound.

For example, contaminating baculovirus may be removed from a recombinant protein being expressed in insect cells by separating cells from its culture fluid by centrifugation (5 min. at 1000 g). The cell supernatant at this point contains both recombinant protein and the contaminating baculovirus. To remove the contaminating virus, the cell supernatant is first filtered (0.2 μm) to remove cellular debris. The filtered cell supernatant, which still contains contaminating viruses, is then passed directly over a resin column as described in Example 2. As a result, the baculovirus binds to the column matrix and the desired protein passes through the column matrix. At this point, the viral-free protein may be further purified using standard chromatographic techniques, including DEAE or gel filtration chromatography. The removal of contaminating baculovirus may be confirmed using assays such as those described in the Examples.

Further, baculovirus may be separated from contaminating proteins in, for instance, an insect cell line. Baculovirus can be used to express heterologous protein in insect cells. The protein is purified away from the insect cells and the present procedure is then used to bind out and concentrate the baculovirus away from the insect cells by collecting the virus with the cell supernatant. The collected supernatant is first filtered (0.2 μm) to remove cellular debris and then is passed directly onto the resin matrix as described in Example 1. We have found that contaminating proteins in the cell free supernatant, have surprisingly little effect on baculoviral binding (Example 3). Following sample application, the column is washed with an appropriate buffer to remove the remnants of the non-binding proteins. The viruses are then eluted from the column by using a solution having a pH different than the pH of the cell supernatant. The collected viral vector can then be further purified by conventional methods.

In the most preferred methods, an ion exchange chromatography resin is prepared using a first buffer having a first pH value. Next, the preparation is loaded onto the resin and optionally, the resin is washed with the first buffer following loading of conditioned medium. The baculovirus is removed from the ion exchange resin by loading a second buffer onto the resin having a second pH value that is different than the first pH value. Preferably, the buffers are organic buffers and for a cation exchange resin, the pH value of the first buffer is less than that of the second buffer, whereas for an anion exchange resin, the pH value of the first buffer is greater than that of the second buffer.

C. Other Factors

Temperature may play a significant role in the method and we have found that a temperature of 4° C. is optimal. We have also found that column geometry exerts a significant effect on the effectiveness of a column to concentrate virus. Longer and narrower columns (length/width ratio of >4) are preferred over short, narrow columns (length/width ratio of 1–3) See Example 5.

It should be noted that many other brands and sizes of chromatography column could also be employed and persons having ordinary skill in the art using generally available knowledge and the teachings herein, would readily understand the procedures for testing whether, and to what extent, a particular column material and column geometry will concentrate baculovirus.

D. Viral assays

Baculoviral assay systems are described in O'Reilly, D. R., Miller, L. K., and Luckow, V. A. (1992) *Baculovirus Expression Vectors: A Laboratory Manual*. (Freeman, New York); Kitts, P. A. and Possee, R. D. (1993), supra. Beta-galactosidase assays are described in Boyce, F. M. and Bucher, N. L. R. (1966), supra. Baculovirus can be quantified in several ways. One standard assay is to quantitate the virus in terms of plaque forming units by virtue of their ability to form plaques by lysing cells within a lawn of susceptible insect cells (O'Reilly et al., supra). Another method relies on the ability of baculovirus to transfer an easily quantifiable reporter gene, such as the lacZ gene which encodes the calorimetric enzyme β-galactosidase, into insect or mammalian cells. Beta-galactosidase activity can be quantitated in terms of the percentage of cells expressing the protein (and, therefore, turn blue upon incubation with a specific reagent) or in terms of the total amount of β-galactosidase activity in the cell population.

The invention will now be illustrated by the following non-limiting Examples.

EXAMPLE 1

Aggregation of Baculovirus During Gradient Purification

This example illustrates that baculoviruses will aggregate into large clumps whenever prior art ultracentrifugation/ gradient concentration methods are used.

Z4 conditioned medium is loaded into SW28 ultracentrifuge tubes (33 ml per tube) and underlayered with 3 ml per tube 27% sucrose in 10 mM Tris pH 7.5 and 1 mM EDTA ("TE"). The virus is pelleted through this sucrose cushion by ultracentrifugation at 24,000 rpm for 75 minutes using an SW28 rotor. The virus pellet is gently resuspended overnight at 4° C. in 0.3 ml TE per tube. This virus resuspension is then loaded onto a 20–60% sucrose gradient in TE in SW41 ultracentrifuge tubes and banded by ultracentrifugation at 38,000 for 75 minutes. The opalescent virus band is collected by side puncture with a 20 g needle. About 0.5 ml is collected per tube. The virus fraction is pooled, diluted with TE to a final volume of 10 ml and then pelleted in two SW50.1 ultracentrifuge tubes at 30,000 rpm at 4° C. for 60 minutes. The virus pellet is resuspended overnight in 0.2 ml PBS at 4° C.

We found that Z4 and other baculoviruses aggregate into large clumps which are visible by eye whenever the above ultracentrifugation/sucrose gradient purification is performed. We found that about 99.9% of Z4 concentrated by this method is pelleted by spinning at 4000 g for 6 minutes. Less than 25% of the starting virus is pelleted at this low speed. Further, the virus also lost some infectivity after ultracentrifugation (data not presented).

Although these baculovirus aggregates appear to break up to some extent after the virus is incubated in mammalian cell culture medium at 37° C., the presence of virus in aggregates may prevent its effective transduction of mammalian cells and tissues after administration in vivo. These aggregates may be too large to penetrate the narrow passages, such as the hepatic sinusoids, through which the virus must pass in order to reach the target cells such as hepatocytes. Table 2 illustrates that the presently claimed chromatography procedure does not lead to baculovirus aggregation.

EXAMPLE 2

Use of Cation Exchange Column

Z4 is produced in Sf9 insect cells grown in serum-free medium (Sf-900 II SFM; obtained from GibcoBRL, Gaithersburg, Md.). Serum-free medium may be used so that the total amount of protein in the conditioned medium will be low. If the virus is produced in serum-containing medium, the high concentration of bovine serum albumin and other proteins might bind to the column and decrease the binding capacity of the virus. However, we have found that the present column chromatography procedure will work even if other medium is used, including serum-containing medium. In one case, Grace's insect medium plus 10% fetal bovine serum (both GibcoBRL) was employed and rBV was successfully concentrated (Example 3). This may be due to the fact that a minority of proteins (about 10%) will bind to the cation exchange columns that we used.

A. CULTURE CONDITIONS AND MEDIA:

To insure high column binding capacity, serum-free medium is preferred. Sf9 cells are grown in Sf-900 II SFM in 100 ml spinner culture vessels (Corning). Propagation and infection are performed in a 28° C. incubator (Fisher). Cells are infected at a density of $2.0 \times 10^6$ cells/ml with Z4 at a multiplicity of infection (moi) of 2.0 (this indicates 2 virus plaque forming units (pfu) per Sf9 cell. Cells have also been infected in conventional tissue culture flasks with success. Four days after infection, the culture is withdrawn from the spinner vessels. The cells and debris are pelleted by centrifugation in a Beckman J-6M centrifuge at 2500 rpm for min at 4° C. The supernatant, which contains the virus, is removed and either used immediately or stored at 4° C. in the dark for later concentration.

The plaque titer of these preparations is determined by conventional plaque assays in Sf9 cells. The titer in all cases is between $7.5 \times 10^7$ and $2.4 \times 10^8$ pfu/ml.

B. COLUMN PREPARATION:

In this example, a small-scale 1 ml SP column (SP Sepharose Fast Flow; Pharmacia Biotech; cat. #714-7065-00) is used. The SP column is prepared according to the manufacturer's instructions. All column steps take place at 4° C. Briefly, a small volume (~6 ml) of the SP Sepharose is withdrawn from the original container. Since the SP Sepharose is supplied in a pre-swollen 20% ethanol, 0.2M sodium acetate solution, the withdrawn solution is allowed to sit in a 15 ml tube for ~30 min to allow the Sepharose to settle. The ethanol-containing liquid is then withdrawn from above the SP Sepharose. The SP Sepharose is equilibrated by addition of 1 volume of 25 mM MES, pH 5.8 to 3 volumes of packed SP Sepharose. This gel slurry is gently mixed by pipetting and a portion of the slurry is then poured into a 0.8×4 cm disposable plastic column (a BIO-RAD poly-prep chromatography column; cat. #731-1550; BIORAD, Hercules, Calif.) with 1.0 ml of packed SP Sepharose eventually formed. Immediately after pouring the column, a large excess of 25 mM MES, pH 5.8 is loaded onto to column and the SP column is washed with this buffer for ~60 min. The column could be poured on the day of the concentration or on an earlier day.

C. ELUTION/CONCENTRATION:

Conditioned medium containing rBV is loaded onto the column and the flow-through allowed to pass. In Table 1, a total of 30 ml of conditioned medium is added to a 1 ml column. After every 7.5 ml of loading volume, a fresh collecting tube is used. Therefore, tubes FT1, FT2, FT3 and FT4 indicate the flow-through after 7.5, 15, 22.5 and 30 ml of conditioned medium is loaded. We did not wash the column following loading of conditioned medium, but if we had done so, we would use 25 mM MES buffer, pH 5.8.

To elute the virus from the column, 1.6 ml of PBS (phosphate-buffered saline, pH 7.4; GibcoBRL, cat. #10010-015) is added. The pH is critical, in that the virus elution from the column is driven by the increase in pH. After loading the PBS, small volume fractions are collected. After the PBS elution, PBS having NaCl at a final concentration of 0.5 M is loaded onto the column to determine if this higher salt concentration could be used to elute more virus.

D. VIRAL ASSAY:

Baculovirus can be assayed in the flow-through and elution fractions in two ways. The plaque titer is determined by a conventional plaque forming assay in Sf9 cells . See O'Reilly, D. R., Miller, L. K., and Luckow, V. A. (1992) *Baculovirus Expression Vectors: A Laboratory Manual*. (Freeman, New York); Carrascosa, A. L. (1994) "Enhancement of baculovirus plaque assay in insect cells by DEAE-Dextran". BioTechniques 16, 1078–1085. In this case, X-gal (5-bromo-4-chloro-3-indolyl-β-galactopyranoside; Sigma, St. Louis. Mo.) is added to the agarose overlay at a final concentration of 0.15 mg/ml to allow for easier plaque detection. At seven days post-infection, plaques are counted.

The second assay is the transduction of the human hepatoma cell line HepG2 (ATCC; the human hepatoma cell line HuH7 is also used in some cases with similar results) and quantitation of β-galactosidase expression levels. This latter assay is done in one of two ways. For a visual assay:

1. Seed $2 \times 10^5$ HepG2 cells per well into multiple wells of 12-well tissue culture dishes (Corning, cat. #25815; Corning, N.Y.) in DMEM plus 10% fetal bovine serum (GibcoBRL).
2. After the cells have firmly attached to the plate, add known volumes of starting virus and column fractions.
3. 18–24 hours later, rinse the wells once with PBS.
4. Fix the cells by addition of cold 2% formaldehyde/0.2% glutaraldehyde in PBS, 5 min 4° C.
5. Wash 3 times over 10 min with PBS/2 mM $MgCl_2$
6. During the washes, dilute and filter the X-gal stock (the stock is 40 mg/ml X-gal in dimethlyformamide) by diluting the X-gal to 1 mg/ml final in 5 mM ferricyanide, 5 mM ferrocyanide, 2 mM $MgCl_2$, 1×PBS and filtering through a 0.4 μm filter.
7. Add diluted X-gal to wells and incubate at 37° C. for 5–24 hr (reaction is completed by ~5 hr).
8. Determine the percentage of β-galactosidase positive cells (blue cells) by counting under a microscope.

An alternative, more quantitative, assay is a chemiluminescent β-galactosidase assay. In this case, cells are seeded and treated with virus as described above. On the next day, cell lysates are taken and β-galactosidase activity quantitated by a luminescent β-galactosidase assay (CLONTECH; catalog #K2048-1; Palo Alto, Calif.) according to the manufacturer's instructions.

RESULTS

The results of one column chromatography experiment are shown in Table 1.

TABLE 1

S Sepharose Column Chromatography of rBV Z4

| Sample | β-Gal activity |
|---|---|
| 1.0 ml S column, loaded 30 ml Z4 | |
| a. starting virus | 1.000 |
| b. pre-load column wash | 0.002 |
| c. FT1 (after 7.5 ml loaded) | 0.062 |
| d. FT2 (after 15 ml loaded) | 0.441 |
| e. FT3 (after 22.5 ml loaded) | 0.486 |
| f. FT4 (after 30 ml loaded) | 0.458 |
| add 1.6 ml PBS | |
| g. FT5 (first 0.3 ml) | 0.540 |
| h. E1 (next 0.3 ml) | 4.852 |
| I. E2 (next 0.5 ml) | 91.792 |
| j. E3 (next 0.7 ml) | 0.914 |
| add 2.0 ml PBS/0.5 M NaCl | |
| k. E4 (next 2.0 ml) | 0.043 |

In this case, the virus is quantitated by β-galactosidase expression in transduced HepG2 cells. The numbers in Table 1 are relative β-galactosidase levels, with 1.0 corresponding to the β-galactosidase level in cells treated with the starting virus. All other number refer to the β-galactosidase level in HepG2 treated with an equal volume of the various fractions. There is no detectable β-galactosidase activity in untreated cells or in cells treated with the column wash prior to the loading of the virus. Virtually all of the first 7.5 ml of virus bound to the column, as judged by the very low β-galactosidase level of cells infected with FT1. As the next 22.5 ml of virus is loaded, some material bound to the column and some flowed through (see results with fraction FT2-4). These results indicate that the virus bound very well to this column at the low pH. In all columns done subsequently, we have loaded a volume of conditioned medium between 10 and 30 times the column size (for instance, as we scaled up to a 10 ml column, we loaded a total of 200 ml of conditioned medium).

After loading the elution buffer (PBS), the first 0.3 ml is still flow-through. In the next 0.3 ml, the virus clearly is starting to be concentrated. Most of the elution virus appeared in one sharp peak fraction (E2). In this fraction, the concentration of virus is increased 90-fold over the starting virus. In our experience, the virus concentration is commonly between 30- and 100-fold. Since the volume of virus decreases 60-fold (from 30 ml of starting virus to 0.5 ml virus elution volume), the maximum theoretical increase in virus titer is 60-fold. Nevertheless, the procedure results in an increase in titer from 30-fold to as much as 100-fold. The reason for an increase in viral concentration above the theoretical maximum of 60-fold is not presently known, but it could be due to increased virus activity in PBS relative to its activity in the original medium or to the removal by this method of agent(s) present in the virus preparation which inhibit virus activity.

Loading the column with PBS/0.5 M NaCl did not elute any more virus. Both this high salt treatment and a quantitation of the amount of virus in fraction E2 relative to the amount in the load and in the flow-through fractions indicate that virtually all of the Z4 virus is eluted from the column in PBS. Since this is a physiological buffer, the elution fraction can be directly added to cultured cells or injected into animals without toxicity.

An advantage to using an SP column is that only a low percentage of total protein (~10%) will bind to this column. Thus, this one step will produce a concentrated rBV with very little contaminating protein.

Quantitation of the virus in the column fractions by plaque assays precisely agreed with the β-galactosidase assays. For the material shown in Table 1, the starting virus titer (the titer of the conditioned medium) is $8 \times 10^7$ pfu/ml. The titer in fraction E2 is to $7 \times 10^9$ pfu/ml. In a larger scale concentration, 200 ml of conditioned medium is loaded onto a 10 ml SP column. The starting virus titer is $1.7 \times 10^8$ pfu/ml. The peak elution fraction had a titer of $8 \times 10^9$ pfu/ml. The rBV virus is chromatographically concentrated in that it had been concentrated by a factor of at least five over a concentration of baculovirus prior to the chromatographic procedure.

As stated above (See Example 1), concentration of rBV by ultracentrifugation and sucrose gradient banding tended to cause aggregation of the virus. To assay virus aggregation, we performed a low speed centrifugation (4000 g for 6 minutes in a table-top Eppendorf microfuge) followed by a β-galactosidase assay of HepG2 cells treated with samples of the supernatant. We found that rBV concentrated by ultracentrifugation is virtually completely pelleted by this low speed spin (99.9% of virus in the pellet), indicating that it is aggregated into significantly large clumps (data not shown). The present chromatography procedure does not lead to baculovirus aggregation, as presented below in Table 2.

TABLE 2

Virus aggregation in Fast S column fractions

| Sample | β-Gal activity | % soluble |
|---|---|---|
| 1.0 ml S column, loaded 30 ml Z4 | | |
| a. starting virus | 1.000 | 68.7 |
| b. pre-load column wash | 0.002 | – |
| c. FT1 (after 7.5 ml loaded) | 0.062 | 0 |
| d. FT2 (after 15 ml loaded) | 0.441 | 54.9 |
| e. FT3 (after 22.5 ml loaded) | 0.486 | 67.9 |
| f. FT4 (after 30 ml loaded) | 0.458 | 45.4 |
| add 1.6 ml PBS | | |
| g. FT5 (first 0.3 ml) | 0.540 | 61.1 |
| h. E1 (next 0.3 ml) | 4.852 | 69.3 |
| I. E2 (next 0.5 ml) | 91.792 | 76.8 |
| j. E3 (next 0.7 ml) | 0.914 | 100.0 |
| add 2.0 ml PBS/0.5 M NaCl | | |
| k. E4 (next 2.0 ml) | 0.043 | 95.4 |

In Table 2, the "percent soluble" data refers to that percent of Z4 remaining in the supernatant following the low speed spin, as determined by HepG2 transduction and β-galactosidase assay of the same samples as those shown in Table 1. Some of the starting virus (~30%) is lost in the pellet during this centrifugation. The column protocol did not cause any apparent increase in virus aggregation, as the percentage of virus in the supernatant following centrifugation of E2 is actually slightly higher than in the starting virus.

EXAMPLE 3

Concentration From Serum-containing Medium

It is preferable to concentrate the virus via column chromatography by starting with virus-containing medium which is serum-free. This is because the high total protein content of medium containing 10% fetal calf serum could result in binding of serum proteins to the column and reduction in the amount of viral binding. In practice, however, we have been able to concentrate virus by SP Sepharose column chromatography using either serum-free or serum-containing conditioning medium. We tested purification of Z4 produced in Sf9 cell in serum-containing medium (Grace's insect medium plus 10% fetal bovine serum). Except for the use of serum-containing medium, the viral production and column chromatography steps are performed as indicated in Example 1. The Z4 virus is concentrated 11.4-fold by our method. This is a lower value that that seen for Z4 produced in serum-free medium and further indicates that, although it is possible to concentrate virus in serum containing medium, serum proteins may lower the virus binding capacity of the column.

EXAMPLE 4

Degree of Purification

According to the present invention, virus should be purified away from contaminating proteins which are either present in the serum-free medium formulation or are secreted from the insect cells during virus production. To determine the degree to which virus is purified away from some of these contaminants, the following experiment was performed.

Baculovirus produced in serum-free medium is concentrated by column chromatography using a CM Sepharose column. The CM column (CM Sepharose Fast Flow; Pharmacia Biotech, Inc., cat. #17-0719-01) is one of several cationic exchange columns that we have used. CM is a weaker cation exchanger that SP. In this instance, the viral titer was increased 23.4-fold by the column chromatographic methods of the invention.

Equal amounts of plaque forming units of the unconcentrated virus (prior to the column) and the concentrated virus (after the column) are aliquoted, and the concentrated virus is diluted in PBS to the same final concentration as the unconcentrated virus ($1 \times 10^8$ pfu/ml). Twenty ml of each sample ($2 \times 10^9$ pfu) are pelleted by ultracentrifugation through a 27% sucrose cushion (SW41 rotor, 38,000 rpm for 75 minutes at 4° C.). The baculovirus should be pelleted by this centrifugation, while soluble proteins would be present in the supernatants. The virus in the pellet is resuspended and tested for transduction of human hepatoma cells.

The results indicate that equal amounts of virus are present in the pellets of the two samples (concentrated and unconcentrated virus). The total amount of protein in the supernatants is determined by use of a Coomassie Plus Protein Assay Test (Pierce , Cat. #30 23236). The total amount of protein in the sample from the concentrated virus is 58 ug/ml while the total protein in the unconcentrated virus is 380 ug/ml. This indicates that 85% of total protein is removed from the conditioned medium by the column chromatography. Since 100% of the baculovirus may not be pelleted by the ultracentrifugation step and since some of the protein in the supernatant may be viral proteins that were lost from the virions, some of the total protein in the supernatant may actually be of baculoviral rather than contamination origin. Thus, greater than 85% of the non-baculoviral protein may be removed by chromatography.

EXAMPLE 5

Effect of Column Geometry

We also have found that the geometry of the column used in the present method affects the degree of concentration achieved. Long, thin columns (having an internal diameter/length ratio of at least 4:1) are preferred to those having lower ratios, although both have been used with success. As an example, baculovirus Z4 is concentrated using two different column sizes. In each case, the total SP Sepharose is 6.0 ml. This amount of resin is poured into a column having an internal diameter of 1.5 cm (BIO-RAD; cat #732-1010). The height of the resin bed is 3.5 cm. Six ml of resin is also introduced into three, 2.0 ml columns in parallel, each having an internal diameter of 0.8 cm (BIO-RAD; cat #731-1550) and a individual column height of 3.8 cm (total column height 11.4 cm). Simultaneously, 120 ml of Z4-conditioned medium is loaded onto the single 1.5 cm-wide column and the three, 0.8 cm-wide columns (40 ml per column). The virus is eluted with PBS. The virus-containing elution fractions from the three narrow columns are one-third the volume of the elution fractions from the one wider column. Thus, after pooling the fractions from the three narrower columns, the elution volumes were the same as the one wide column. Z4 is concentrated roughly 38-fold through use of the three narrow columns, but only 15-fold in the wider column. Although this experiment is not precisely quantitative and controlled (i.e., the flow rates of the different sized columns was not equal), the clear result is that longer, thinner columns are preferred.

EXAMPLE 6

Use of Anion Exchange Columns

Although SP column chromatography has been very successful, we also have concentrated Z4 virus through use of a Q Sepharose Fast Flow column (Pharmacia Biotech; cat. #71-7070-00), which is a strong anionic exchanger. In this case, the column is equilibrated with 25 mM HEPES, pH 7.5. The pH of the conditioned medium is raised by addition of 0.25 M HEPES, pH 7.5 to a final concentration of 25 mM. Elution of the virus is performed at low pH by the addition of 25 mM MES pH 5.9, 0.15 M NaCl. In the one trial of this column, a six-fold concentration of virus is achieved. This may not be the preferred method since the degree of viral concentration was less than that found with cationic exchange columns and more of the medium components bind to the Q column as compared to the SP column.

EXAMPLE 7

Alternate Resin Compositions

Below are five examples of some alternative resins that we used successfully to concentrate baculovirus.

We used baculovirus Z4. The organic buffer MES, pH 5.8, is added to the Z4-conditioned medium to a final concentration of 25 mM. Five different 1.0 ml columns are poured as described in Example 1 and equilibrated with 25 mM MES (pH 5.8). Fifteen ml of Z4 is loaded onto each column and the bound virus eluted with PBS, with three 0.6 ml fractions taken in each column. The five columns were as follows:

1. Bakerbond™prepscale Abx (J. T. Baker; cat. # 7269-02). This is a mixed resin column. The support is silica while the functional groups are mixed. In this column, both cationic and anionic groups may bind.
2. Bakerbond™wide-pore prepscale Carboxy-sulfon TM (J. T. Baker; cat. # 7252-00). This is another mixed resin consisting of both carboxyl and sulfate functional groups. The solid support is silica.
3. Whatman CM23. This resin is cellulose with a carboxymethyl functional group.

4. Trisacryl® M (LKB[France]; cat #22-5-100). This resin also has a carboxymethyl functionality but has an acrylamide support.
5. BioRad Macro-prep® High S Support (BioRad; cat#156-0030). This resin is a ceramic support with strong cation exchange properties, probably due to sulfate functional groups.

All these columns were successful in concentrating baculovirus. We observed considerable variation in flow rates among the columns; the CM23 column ran very fast while the BioRad column ran slowly. The other columns had intermediate flow rates. The virus eluted in slightly different fractions in the different columns. The virus was most concentrated in the first 0.6 ml elution fraction in the Trisacryl® column, in the second elution fraction in the Abx, CM23 and Macro-prep® High S columns, and in the third fraction in the Carboxy-sulfon™ column. All methods produced at least a 6-fold increase in baculovirus titer.

Of these five columns, the highest virus concentration occurred using the Bakerbond™ prepscale Abx. In this column, the baculovirus titer in PBS elution fraction #2 was 15.6-fold higher than the starting viral titer. It would be routine to develop a greater degree of virus concentration by optimizing chromatography protocols with these columns. For example, in all of the columns except the CM23 column, there was virtually no virus appearing in the flow-though. This indicates that virus binding was very efficient and that a greater degree of virus concentration may be achieved by simply loading more virus on the columns.

Equivalents

From the foregoing, it will be evident that, although specific embodiments of the invention have been described herein for purposes of illustration, various modifications may be made without deviating from the spirit and scope of the invention.

What is claimed is:

1. A process for producing chromatographically concentrated baculovirus which comprises (a) contacting a preparation containing a baculovirus with an ion exchange chromatographic resin containing a first buffer, under conditions and for a time sufficient for the virus to bind to the resin; and (b) eluting the bound baculovirus from the resin in concentrated form.

2. The process of claim 1, further comprising optionally washing the resin with a second buffer prior to the eluting step, the second buffer being substantially identical to the first buffer.

3. A method for the concentration of a baculovirus from contaminating substances, comprising the steps of: (a) contacting a preparation containing a baculovirus with an ion exchange chromatographic resin, under conditions and for a time sufficient for the baculovirus to bind to the resin; and (b) eluting the bound baculovirus from the resin, thereby recovering the baculovirus.

4. The method of claim 3, wherein the step of contacting comprises contacting with a resin that is a cation exchange resin.

5. The method of claim 3, wherein the step of contacting comprises contacting with a resin that is an anion exchange resin.

6. The method of claim 3, wherein the step of eluting comprises eluting the bound baculovirus by contacting the resin with physiological salt solutions of successively differing pH values.

7. The method of claim 3, wherein the preparation comprises a fluid that contains serum.

8. The method of claim 3, wherein the preparation comprises a fluid that lacks serum.

9. A method for the removal of a baculovirus from a preparation containing a baculovirus, the method comprising the steps of: (a) contacting the preparation with an ion exchange chromatography resin, under conditions and for a time sufficient to permit said virus to bind to said resin; and (b) separating the portion of the preparation which is not bound to said resin from said resin.

10. The method of claim 9, wherein the step of contacting comprises contacting with a resin that is a cation exchange resin separating.

11. The method of claim 9, wherein the step of contacting comprises contacting with a resin that is an anion exchange resin.

12. A method for purifying a baculovirus from a preparation containing a baculovirus, the method comprising the steps of: (a) preparing an ion exchange chromatography resin using a first buffer having a first pH value; (b) loading the preparation onto the resin; (c) optionally washing the resin following loading of conditioned medium with the first buffer; (d) removing the baculovirus from the ion exchange resin by loading a second buffer onto the resin having a second pH value that is different than the first pH value.

13. The method of claim 12, wherein the first buffer is an organic buffer having pH value of about 5.8 and the second buffer is an organic buffer having a pH value of about 7.4.

14. The method of claim 12, wherein the resin is a cation exchange resin comprising sepharose derivatized by aryl sulfate groups or sulfonic acid groups.

15. The method of claim 12, wherein the first buffer is an organic buffer having a pH of about 7.5 and the second buffer is an organic buffer having a pH of about 5.9.

16. The method of claim 15, wherein the resin is an anion exchange resin comprising sepharose derivatized by quaternary amine groups or quaternary aminoethyl groups.

17. The method of claim 15, wherein the first buffer is HEPES, pH 7.5 and the second buffer is MES pH 5.9

18. The method of claim 12, wherein the step of preparing a resin comprises preparing an ion exchange resin selected from the group consisting of: (i) a mixed resin column of silica derivatized with mixed cationic and anionic groups; (ii) a silica resin comprising carboxyl and sulfate functional groups; (iii) a cellulose resin with carboxymethyl functional groups; (iv) an acrylamide resin with carboxymethyl functional groups; (v) a ceramic resin with sulfate functional groups; and (vi) a sepharose resin with carboxymethyl functional groups.

19. A chromatographically concentrated preparation of active baculovirus having the following properties: (a) concentrated at least five fold from an original preparation; (b) having less than 50% of total soluble protein, exclusive of viral protein, and (c) in contact with a physiological buffer.

20. A chromatographically concentrated preparation of active baculovirus having the property of lacking significant aggregation when tested by centiifugation at about 4000 g for about 6 minutes.

21. A preparation of chromatographically concentrated active baculovirus, prepared by the process of claims 1, 3 or 12.

* * * * *